United States Patent [19]

Fowler

[11] Patent Number: 5,108,421
[45] Date of Patent: Apr. 28, 1992

[54] INSERTION ASSEMBLY AND METHOD OF INSERTING A VESSEL PLUG INTO THE BODY OF A PATIENT

[75] Inventor: Bradford C. Fowler, Woodinville, Wash.

[73] Assignee: Quinton Instrument Company, Seattle, Wash.

[21] Appl. No.: 591,342

[22] Filed: Oct. 1, 1990

[51] Int. Cl.⁵ .................................. A61B 17/04
[52] U.S. Cl. .................... 606/213; 606/215; 604/15
[58] Field of Search ........ 128/831, 843, 887, 897–899, 128/207.15; 606/213; 604/15, 285–288, 57, 59, 60, 68–70, 73; 600/32

[56] References Cited

U.S. PATENT DOCUMENTS

| | | |
|---|---|---|
| 581,235 | 4/1897 | Kenyon . |
| 1,191,736 | 7/1916 | Roberson . |
| 1,794,221 | 2/1931 | Washburn et al. . |
| 2,898,913 | 8/1959 | Ritter et al. ............ 128/296 |
| 3,056,408 | 10/1962 | Brown ................... 128/325 |
| 3,447,533 | 6/1969 | Spicer ................... 128/1 |
| 3,516,403 | 6/1970 | Cournut ................. 128/130 |
| 3,675,639 | 7/1972 | Cimber .................. 128/1 |
| 3,874,388 | 4/1975 | King et al. ............. 128/334 R |
| 4,007,743 | 2/1977 | Blake .................... 128/334 R |
| 4,154,226 | 5/1979 | Hennig et al. ........... 128/1 R |
| 4,182,339 | 1/1980 | Hardy, Jr. .............. 128/334 R |
| 4,577,631 | 3/1986 | Kreamer ................. 128/334 R |
| 4,587,969 | 5/1986 | Gillis ................... 128/334 R |
| 4,588,395 | 5/1986 | Lemelson ................ 604/59 |
| 4,610,248 | 9/1986 | Rosenberg ............... 128/325 |
| 4,645,488 | 2/1987 | Matukas ................. 604/59 |
| 4,669,474 | 6/1987 | Barrows ................. 128/334 C |
| 4,710,192 | 12/1987 | Liotta et al. .......... 623/1 |
| 4,744,364 | 5/1988 | Kensey .................. 128/334 R |
| 4,774,091 | 9/1988 | Yamahira et al. ........ 424/426 |
| 4,790,819 | 12/1988 | Li et al. .............. 604/59 |
| 4,829,994 | 5/1989 | Kurth ................... 128/96.1 |
| 4,832,688 | 5/1989 | Sagae et al. ........... 604/53 |
| 4,852,568 | 8/1989 | Kensey .................. 128/325 |
| 4,871,094 | 10/1989 | Gall et al. ............ 222/386 |
| 4,890,612 | 1/1990 | Kensey .................. 606/213 |
| 4,929,246 | 5/1990 | Sinofsky ................ 606/8 |
| 5,021,059 | 6/1991 | Kensey et al. .......... 606/213 |
| 5,053,046 | 10/1991 | Janese .................. 606/230 |
| 5,061,274 | 10/1991 | Kensey .................. 606/215 |

FOREIGN PATENT DOCUMENTS 782814 11/1980 U.S.S.R. .

Primary Examiner—Stephen C. Pellegrino
Assistant Examiner—Gary Jackson
Attorney, Agent, or Firm—Andrew J. Beck; Montgomery W. Smith; Richard D. Allison

[57] ABSTRACT

A device and method of closing an incision or puncture in a patient by inserting a vessel plug into the incision or puncture until the distal end of the vessel plug is adjacent to the outer lumen of the blood vessel or target organ so that the vessel plug does not obstruct the flow of fluid through the blood vessel or target organ. The precise positioning of the vessel plug in the incision or puncture is accomplished through the use of a balloon catheter or a cylindrical insertion assembly having a proximal plunger member associated therewith.

19 Claims, 4 Drawing Sheets

INSERTION ASSEMBLY AND METHOD OF INSERTING A VESSEL PLUG INTO THE BODY OF A PATIENT

FIELD OF THE INVENTION

The present invention relates generally to hemostatic devices and more particularly to an insertion assembly and vessel plug which are insertable into an incision or puncture formed in the body of a patient.

BACKGROUND OF THE INVENTION

During catheterization procedures, the nurse or physician will create an opening into an artery or other vessel with a conventional catheter introducer or dilator. The size of the opening will vary depending on the type of procedure and the size of the catheter which is used. For example, the diameter of the catheter and catheter sheath used in standard angiography procedures is typically between 5 to 8 French (1.67 mm and 2.67 mm, respectively). The diameter of the catheter and catheter sheath used in angioplasty procedures may be 8 (2.67 mm) or 9 (3.33 mm) French. The diameter of the catheter and catheter sheath used in intro-aortic balloon pump procedures is typically between 14 to 16 French (4.67 mm and 5.33 mm, respectively) and the diameter of the catheter and catheter sheath used with cardiopulmonary support systems is typically between 18 and 20 French (6.0 mm and 6.67 mm, respectively). Additionally, the catheter is often twisted or otherwise manipulated as it is advanced to the treatment site, thereby causing a further enlargement of the incision or puncture in the body of the patient.

When the medical procedure is completed and the catheter is removed from the artery or other blood vessel, conventional practice has been to apply external pressure to the entry site until clotting occurs. Because many of the patients undergoing these procedures have been medicated with an anticoagulant such as heparin, the nurse may be required to apply external pressure to the incision site for an extended period of time. The time required to stop bleeding at the incision is not an efficient use of the nurses time and a painful hematoma or unsightly bruise may still occur at the incision site because the artery will continue to bleed internally until clotting blocks the opening in the artery.

U.S Pat. No. 4,829,994 granted to Kurth on May 16, 1989 attempts to resolve the above-described problem by providing an apron-like device consisting of a pelvic apron and a groin strap to apply a compressive force to the femoral vessel of the patient. Although this device effectively eliminates the need to have a nurse apply direct pressure to the incision site, the decrease in blood flow through the femoral artery caused by the use of this device may increase the likelihood of thrombosis formation in the compromised patient.

Another approach to resolving the above-identified problem is disclosed in U.S. Pat. No. 4,929,246 granted to Sinofsky on May 29, 1990. The method of using the device disclosed in this patent includes the steps of advancing a semi-rigid tube having an inflatable balloon at its distal end through the overlying tissue to a location adjacent to the outer lumen of the punctured artery. The balloon is then inflated to apply pressure directly to the outer lumen of the artery. Laser energy is then directed to the outer lumen of the artery via an optical fiber centrally located in the semi-rigid tube such that the laser energy passes through the optical fiber and balloon of the semi-rigid tube to thermally weld the artery and seal the incision.

A further approach to resolving the above-identified problems is disclosed in U.S. Pat. No. 4,744,364 granted to Kensey on May 17, 1988 and related U.S. Pat. Nos. 4,852,568 and 4,890,612 granted to Kensey on Aug. 1, 1989 and Jan. 2, 1990, respectively. The first two Kensey patents disclose a device for sealing an opening in the wall of a blood vessel which consists of an elongate tubular body having an expandable closure member removably disposed therein The tubular body also includes an ejecting device disposed within the tubular body for forcing the closure member from the tubular body into the interior of the blood vessel. A retraction filament is secured to the closure member so that the engagement surface of the closure member hemostatically engages the inner surface of the blood vessel contiguous with the puncture. The final Kensey patent discloses a device which includes a plug member having a holding portion which is adapted to engage portions of the tissue adjacent to the punctured vessel or organ to hold the plug member in place and a sealing portion formed of a foam material which extends into the punctured vessel or organ to engage the tissue contiguous therewith to seal the puncture.

None of the prior art devices teach the use of a simple and relatively inexpensive means for effecting the closure of a puncture or incision in the wall of a blood vessel, duct or lumen without extending into the affected blood vessel, duct or lumen.

SUMMARY OF THE INVENTION

Accordingly, it is an object of the present invention to provide a device and method of use which overcomes the disadvantages of the prior art.

It is another object of the present invention to reduce the time required for sealing an incision in an artery and to decrease the likelihood that a hematoma will form after the catheter is removed from the incision.

These and other objects of the present invention are achieved by providing a device and a method for sealing an incision in a blood vessel, duct or lumen using the device as described hereinafter.

One form of the present invention preferably includes a relatively small diameter balloon catheter and a porous, absorbable vessel plug. The vessel plug includes a distal end which is sized and shaped so that the distal end of the vessel plug may be positioned adjacent to the outer surface of the blood vessel duct or lumen and will not cause a disruption in the flow of fluid past the incision. The method of using the preferred form of the present invention includes the steps of inserting the balloon catheter through the previously inserted catheter sheath and then removing the catheter sheath from the incision. The balloon is then inflated and positioned adjacent to the inner wall of the blood vessel, duct or lumen. Next, the vessel plug is inserted into the incision until the distal end of the vessel plug is positioned adjacent to the balloon on the distal end of the catheter The balloon is then deflated and the catheter is removed from the incision. Finally, a dressing may be placed over the incision site to retain the vessel plug in the incision until the vessel plug is incorporated into the surrounding tissue.

An advantage of the present invention is that the distal end of the vessel plug does not extend into the blood vessel duct or lumen and therefore, the flow of fluid through the vessel is not obstructed by the vessel plug and the likelihood that a thrombosis will form at the incision site is reduced.

A further advantage of the present invention is that it is relatively simple to use and the likelihood that a hematoma will form at the incision site is minimized.

DETAILED DESCRIPTION OF THE PRESENT INVENTION

Figure 1:
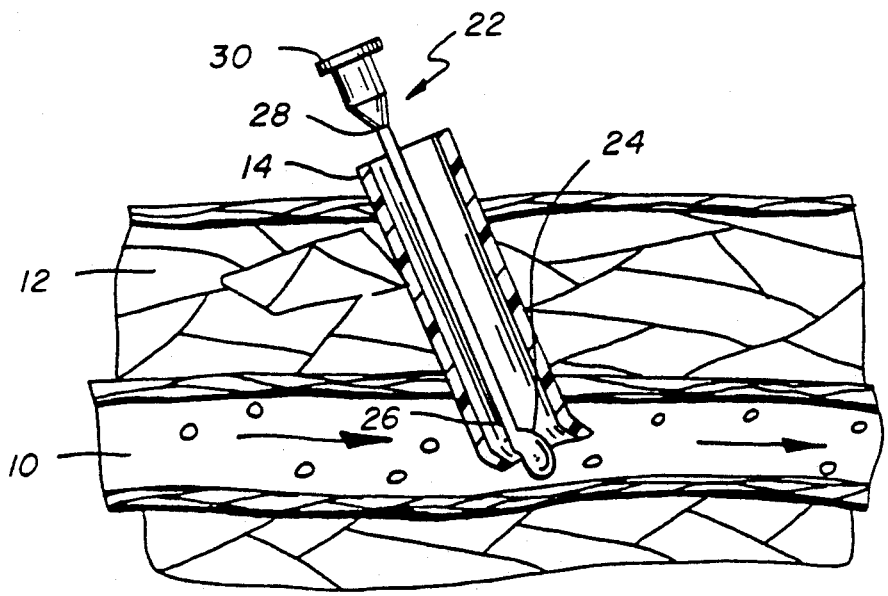
FIG. 1 is a side elevational view, partially in cross section, showing the catheter sheath and balloon catheter of the present invention inserted in the patient.
Figure 2:
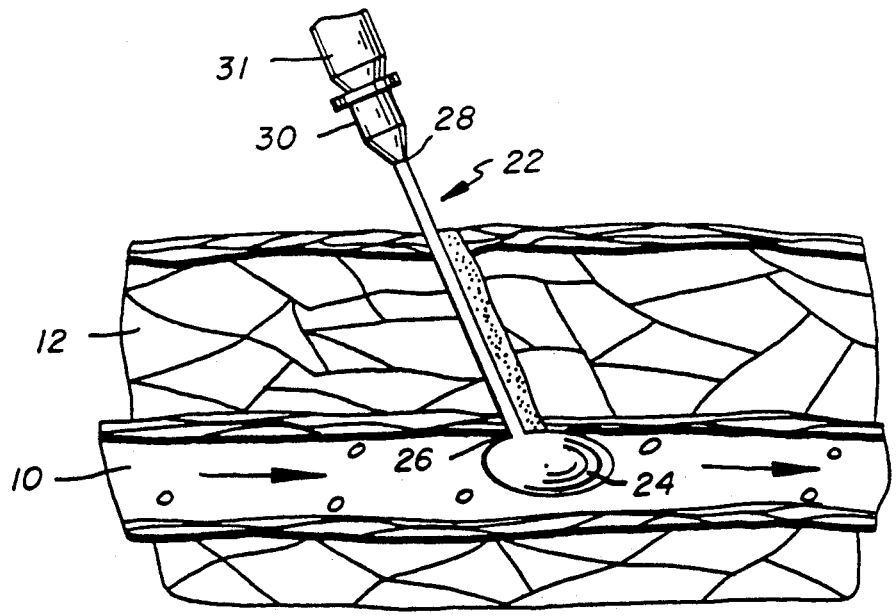
FIG. 2 is a side elevational view, partially in cross section, showing the balloon of the balloon catheter inflated and positioned in the patient.

The present invention is described hereinafter with specific reference to the use of the present invention for sealing an incision or puncture in a blood vessel such as the femoral artery 10 of a patient. It is contemplated that the present invention may be used with nearly any catheterization or other medical procedure wherein it is desirable to seal an incision or puncture to prevent the loss of the patient's body fluid therethrough. As used herein, the distal end of an element is referred to as the end of the element nearest to the patient and the proximal end of an element is referred to as the element furthest away from the patient.

In order to more fully understand and appreciate the present invention, a brief description of a conventional angiographic catheterization procedure through the femoral artery of the patient is set forth herein In such a procedure, an angiographic needle (not shown) is inserted percutaneously through the epidermal and dermal layer of the skin 12 of the patient at a preferred angle of approximately 25 to 45 degrees. The needle is inserted between 6 mm and 70 mm percutaneously into the skin of the patient until the needle pierces the femoral artery. The puncture of the artery 10 by the needle is then confirmed by the physician and a small diameter guide wire (not shown) is inserted through the needle for approximately 15 to 20 cm. The needle is then withdrawn over the guidewire while pressure is applied to the artery 10 to limit the bleeding and prevent the formation of a hematoma at the incision site. The catheter (not shown) and an outer introducer or catheter sheath 14 are inserted over the guidewire and the guidewire is then removed from the inside of the catheter. Next, the catheter is advanced to the final location and the procedure is performed. Once the procedure has been completed, the catheter is removed and only the catheter sheath 14 remains in the incision to allow the vessel plug 20 of the present invention to be inserted into the incision as described hereinafter.

As shown in FIGS. 1-5, the preferred form of the present invention consists generally of a relatively small diameter balloon catheter 22 and the vessel plug 20. The balloon catheter preferably has an outer diameter of 1 mm or less and includes an inflatable balloon 24 on the distal end 26 thereof. The balloon catheter 22 may be constructed of nearly any semi-rigid material such as polyethylene or polyvinylchloride. The balloon catheter 22 includes a proximal end 28 having a syringe attachment 30 thereon. The syringe attachment 30 is designed to receive a liquid or a gas from a syringe 31 which is attachable thereto to allow for the inflation of the balloon as described more fully hereinafter.

Figure 3:
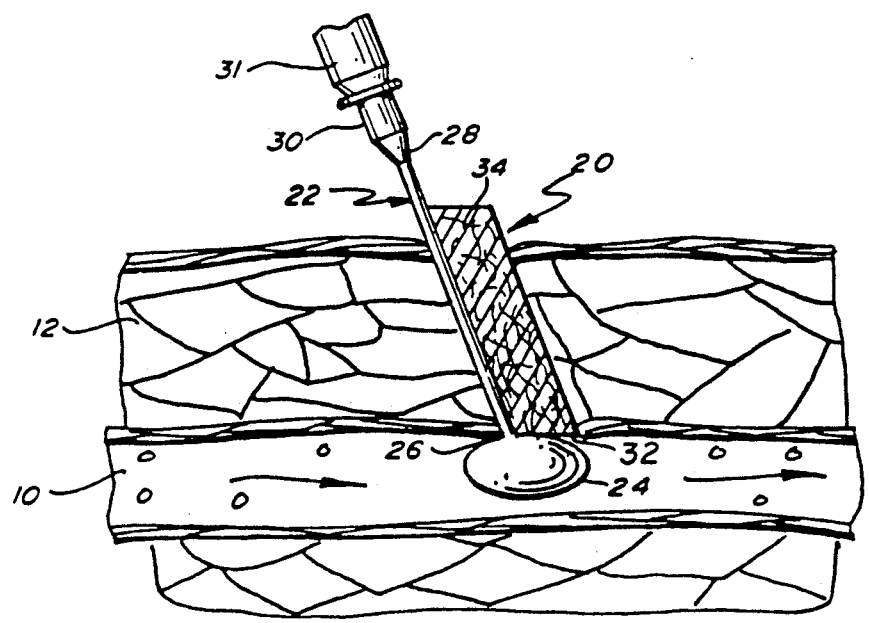
FIG. 3 is a side elevational view, partially in cross section, showing the vessel plug and balloon catheter inserted into the patient.
Figure 4:
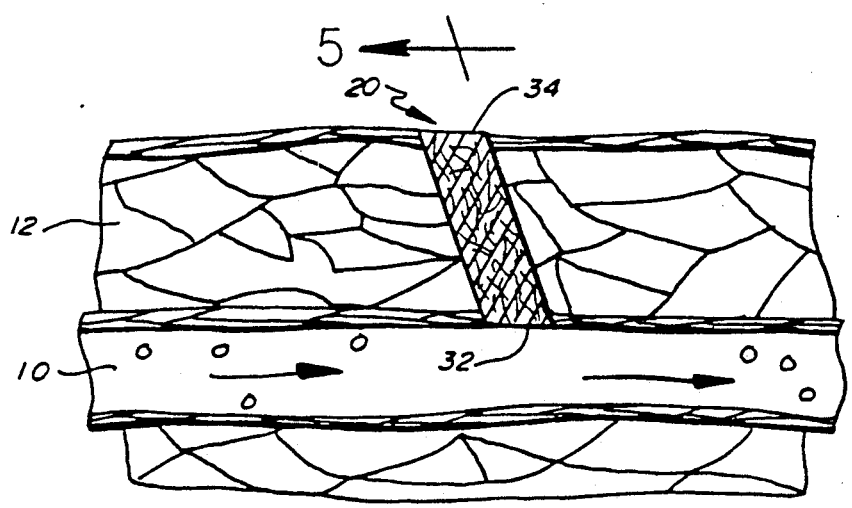
FIG. 4 is a side elevational view, partially in cross section, showing the vessel plug positioned in the patient with the balloon catheter removed.
Figure 5:
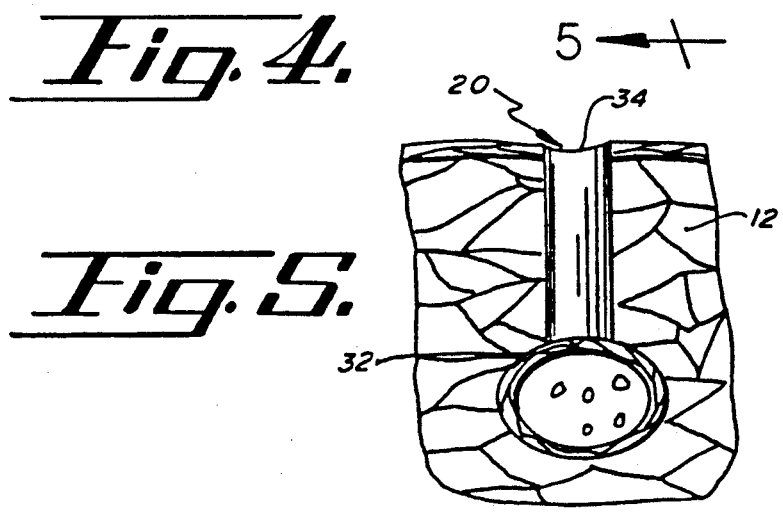
FIG. 5 is a partial side view showing the distal end of the vessel plug of the present invention.

As shown in FIGS. 3-5, the vessel plug 20 of the present invention is preferably a cylindrical rod-shaped member which is constructed of a porous, biodegradable and expandable hemostatic collagen sponge such as the collagen cuff sold by Vitaphore Corporation under the name VITACUFF, or a polymerized polylactic acid, or polyglycolic acid matrix. The distal end 32 of the vessel plug 20 is preferably oriented at an angle of approximately 25 to 45 degrees with respect to the lengthwise dimension of the vessel plug 20 and, as shown in FIG. 5, the distal end 32 of the vessel plug 20 is preferably contoured to conform to the outer lumen of the artery 10. The proximal end 34 of the vessel plug 20 may be excised after placement in the patient and positioned at or slightly below the epidermal layer of the patient's skin as described more fully hereinafter.

Once the angiographic or other medical procedure has been performed and the catheter is removed from the patient, the introducer or catheter sheath 14 remains in the incision as shown in FIG. 1. The catheter sheath 14 functions to maintain the incision open while the balloon catheter 22 is inserted therethrough. Once the balloon catheter 22 is properly positioned in the incision so that the distal end 26 of the balloon catheter 22 extends into the artery 10, the user may withdraw the catheter sheath 14 from around the balloon catheter 22 and out of the incision. The incision will then collapse around the shaft of the balloon catheter and the user may attach a syringe to the syringe attachment 30 on the proximal end 28 of the balloon catheter 22 to inflate the balloon 24. Alternately, the balloon catheter 22 may include an inflation member (not shown) preattached to the proximal end thereof which may be squeezed or otherwise actuated to temporarily inflate the balloon 24. Once the balloon 24 is inflated, the balloon catheter 22 is withdrawn from the incision until the inflated balloon 24 is positioned adjacent to the incision site along the inner lumen of the artery 10. The vessel plug 20 is then inserted into the incision along the shaft of the balloon catheter 22 until the distal end 32 of the vessel plug 20 contacts the inflated balloon 24 on the distal end 26 of the balloon catheter 22. In this position, the distal end 32 of the vessel plug 20 is aligned with the outer lumen of the artery 10 and the balloon 24 prevents the vessel plug 20 from extending into the artery 10. Once the vessel plug 20 is properly positioned in the incision, the balloon 24 is deflated and the balloon catheter 22 is removed from the incision. The user may apply a small amount of pressure to the incision as the balloon catheter is removed to frictionally retaining the vessel plug 20 in the incision. Once the vessel plug 20 is inserted in the incision, the vessel plug 20 will expand as fluids are drawn into the vessel plug 20 from the blood vessels and tissues surrounding the incision and therefore, the contraction of the tissue surrounding the vessel plug 20 along with the expansion of the vessel plug 20 in the incision will assist in retaining the vessel plug 20 in the predetermined position in the incision. The removal of the balloon catheter 22 from the incision will not adversely affect the positioning of the vessel plug 20 because the balloon catheter 22 prevents the portion of the vessel plug 20 adjacent to the balloon catheter 22 from softening and absorbing fluid from the surrounding tissue until the balloon catheter 22 is removed from the incision. As a final step in the insertion of the vessel plug 20 into the incision, the proximal end 34 of the vessel plug 20 which extends beyond the skin 12 of the patient may be excised so that the proximal end 34 of the vessel plug 20 is positioned near the lower portion of the epidermal layer of the skin 12. The opening in the skin 12 may then be sutured closed or have a dressing applied over the incision site.

As described briefly above, the vessel plug 20 of the preferred embodiment initially swells when it is placed in the incision to prevent the formation of a hematoma at the incision site. Additionally, the porosity of the vessel plug 20 may vary depending on the anticipated size of the incision so that the fluids from the surrounding tissue may be absorbed more rapidly if a larger incision is made or if it is necessary for the vessel plug 20 to expand more quickly. Additionally, the porosity of the vessel plug 20 provides the means for connective tissue cell infiltration into the vessel plug 20 so that the patient's tissue will ultimately fill the percutaneous incision at various rates according to the porosity of the vessel plug 20. By positioning the distal end 32 of the vessel plug 20 at or near the outer lumen of the artery 10, there is no disruption of the fluid flow through the artery 10 at the incision site and the risk of thrombosis is minimized as compared to prior devices which include a closure or sealing member which is positioned along the inner lumen of the artery 10. It is anticipated that the vessel plug 20 will degrade and be absorbed within a few weeks or months so that there is no need to remove the vessel plug 20 from the incision at a later date. Additionally, the vessel plug 20 may be formulated to include a conventional clotting agent, such as a tissue thromboplastin, which is incorporated in the collagenous material to accelerate local hematosis and which will allow the physician to maintain the patient on an anticlotting agent such as heparin after the procedure has been performed. It is further anticipated that the vessel plug 20 may be formulated to include a radiopaque material longitudinally incorporated therein to allow the placement of the vessel plug 20 to be observed using conventionally visualization methods.

FIGS. 6-10 illustrate an alternate form of the present invention which consists generally of a preloaded insertion assembly 50 having a vessel plug 52 associated therewith. The insertion assembly 50 of this embodiment consists of a syringe-like device with a plunger 54; a cylindrically shaped outer sleeve 56 and a cylindrically shaped inner sleeve 58. The plunger 54 is preferably sized so that a portion thereof slidably fits within the cylindrical inner sleeve 58. The outer sleeve 56 and the inner sleeve 58 include angled distal ends 62 and 63. The inner sleeve 58 includes a pair of outwardly biased and extending locating wings 64 positioned near the distal end 63 of the inner sleeve 58. These locating wings 64 are biased outwardly and may be opened by withdrawing the outer sleeve 56 from around the distal end 63 of the inner sleeve 58, and closed by the return of the outer sleeve 56 to its original position around the distal end 63 of the inner sleeve 58. Alternately, it is anticipated that the present embodiment may be constructed of one or more cylindrical sleeve members having an actuation member located near the proximal end of the sleeve such that rotation of a lever, rotating handle or other actuation member near the proximal end of the sleeve will cause one or more of the locating wings on the distal end of the sleeve to project radially outwardly from the distal end of the sleeve to temporarily increase the radial circumference of the distal end of the sleeve as the vessel plug 52 is moved to the desired location in the incision.

Figure 7:
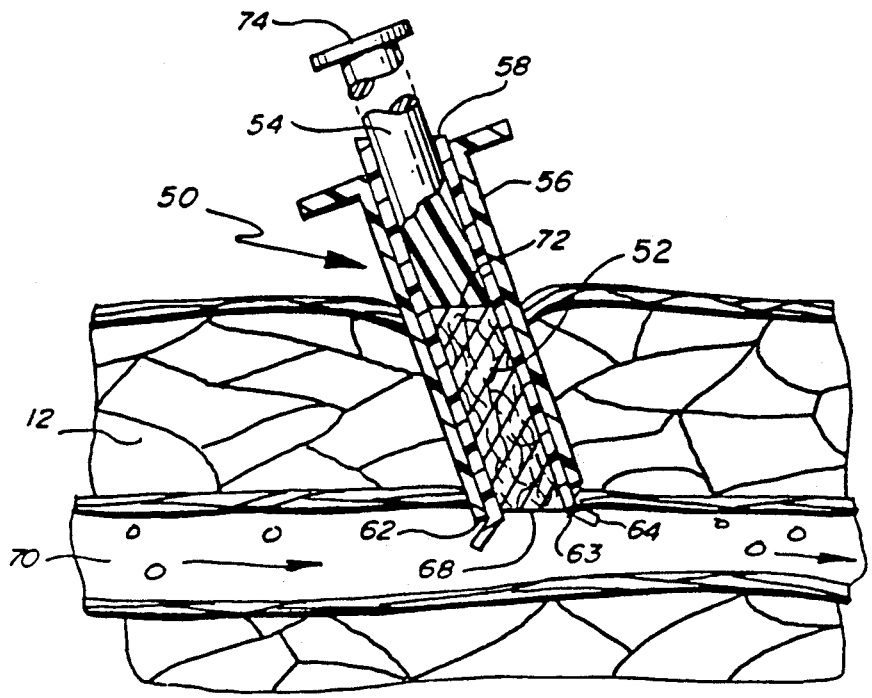
FIG. 7 is a side elevational view, partially in cross-section, showing the introducer assembly of FIG. 6 with the locating wings in the extended position.

The vessel plug 52 of the present embodiment preferably consists of a collagenous material which is formed as a relatively short rod-like member having an angled and contoured distal end 68 which is shaped to conform to the outer contour of the lumen of the blood vessel 70. The proximal end 72 of the vessel plug 52 may be excised after placement and positioned at or slightly below the epidermal layer of the patient's skin, as previously described. In the present embodiment, the vessel plug 52 is positioned in an initial, preloaded condition within the insertion assembly 50 so that the distal end 68 of the vessel plug 52 is located in a predetermined position within the outer and inner sleeves 56 and 58 and adjacent to the locating wings 64 as shown in FIGS. 6 and 7.

The plunger member 54 of the present embodiment is preferably a cylindrically-shaped member which is sized to slidably fit within the inner diameter of the inner sleeve 58. In the initial, preloaded condition, the proximal end of the plunger member 54 extends proximally beyond the proximal ends of the outer sleeve 56 and the inner sleeve 58. The proximal end of the plunger member 54 includes a proximal member 74 thereon which is designed to allow the user to retain the position of the plunger member 54 and the vessel plug 52 in the preferred position within the incision as the inner and outer sleeves 56 and 58 are withdrawn from the incision as described more fully hereinafter.

Figure 6:
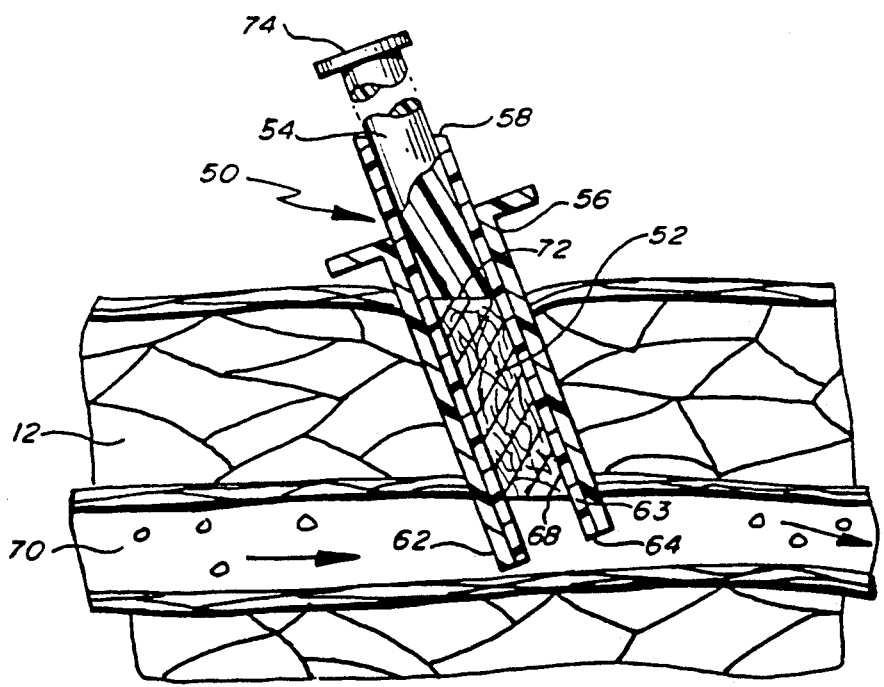
FIG. 6 is a side elevational view, partially in cross-section, showing an alternate form of the present invention once it has been initially inserted into the patient.
Figure 8:
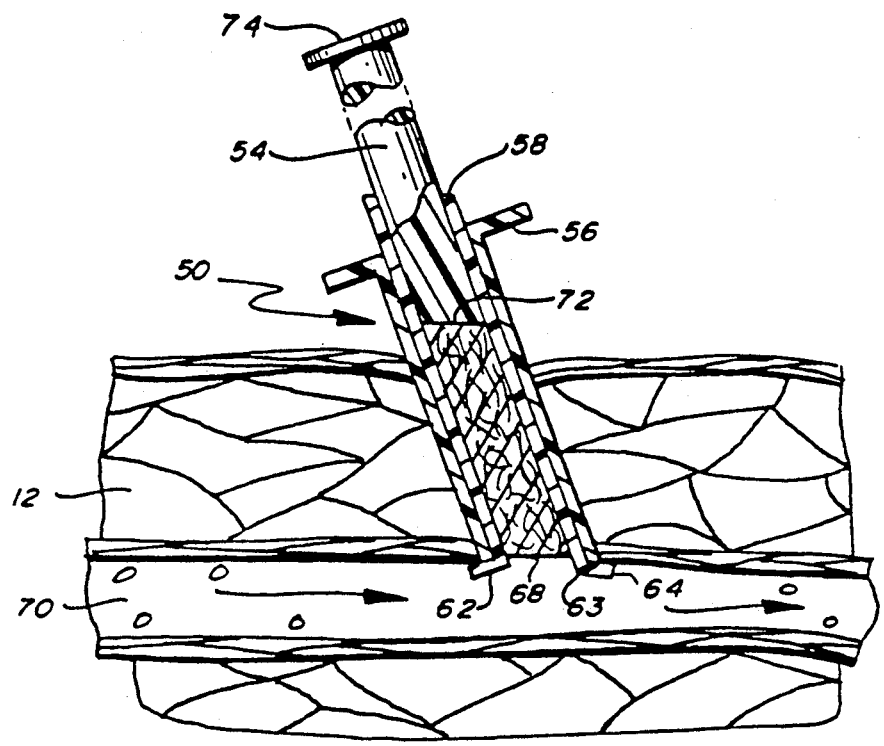
FIG. 8 is a side elevational view, partially in cross section showing the introducer assembly of FIG. 6 with the extended locating wings positioned adjacent to the inner wall of the patient's blood vessel.
Figure 9:
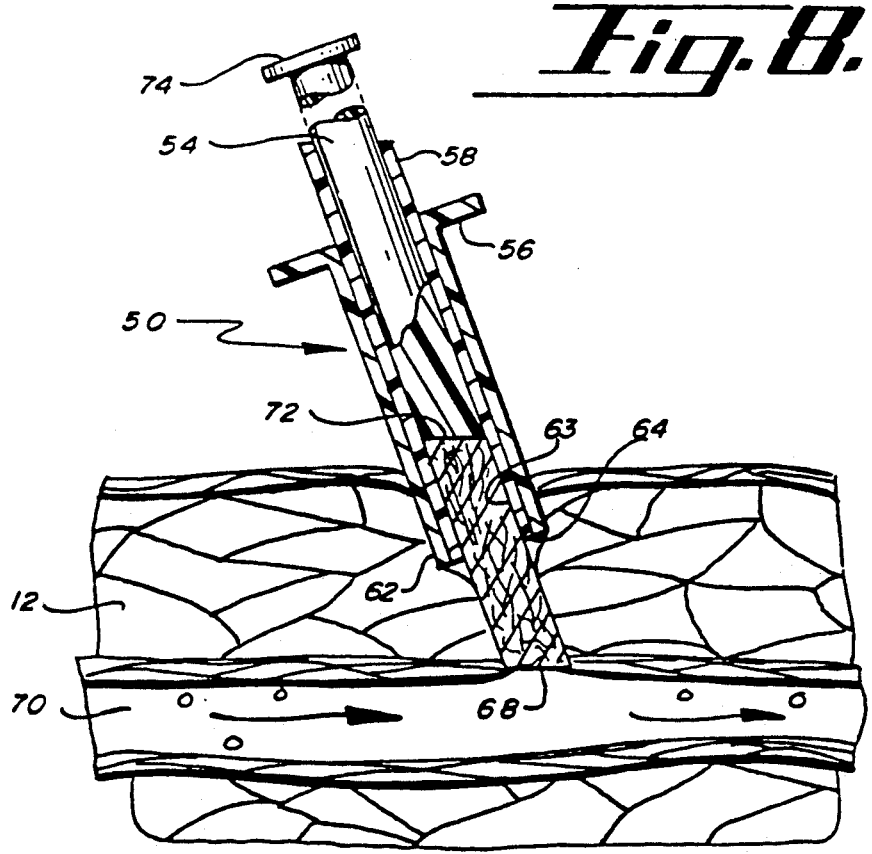
FIG. 9 is a side elevational view, partially in cross section showing the introducer assembly of FIG. 6 after the plunger member and inner and outer sleeves of the introducer assembly have been partially removed from the patient while the plunger is held stationary to retain proper placement of the vessel plug.

As with the preferred embodiment shown in FIGS. 1-5, the alternate embodiment shown in FIGS. 6-10 is used after the medical procedure has been performed. In this embodiment, the previously inserted catheter sheath (not shown) is initially removed while external pressure is applied to the incision to prevent blood loss. The preloaded insertion assembly 50 is then inserted into the incision and blood vessel as shown in FIG. 6. Alternatively, this exchange of catheter assemblies may be facilitated by the use of a guidewire (not shown) which is placed through the catheter sheath prior to its removal from the incision. The insertion assembly 50 may then be subsequently inserted into the incision along or over the guidewire. Once the user verifies that the insertion assembly 50 is fully inserted within the incision and blood vessel 70 as shown in FIG. 6, the user may withdraw the outer sleeve 56 slightly with respect to the inner sleeve 58 to extend the locating wings 64 laterally outwardly from the distal end 63 of the inner sleeve 58. The user may then withdraw the insertion assembly 50 from the incision until the locating wings 64 contact a predetermined portion of the inner lumen of the blood vessel 70 as shown in FIG. 8. The distal end 68 of the vessel plug 52 is particularly positioned in the outer and inner sleeves 56 and 58 and adjacent to the locating wings 64 so that when the locating wings 64 contact the inner lumen of the blood vessel 70, the distal end 68 of the vessel plug 52 is properly aligned in the incision. Next, while holding the plunger member 54 in a fixed position with respect to the patient, the user returns the outer sleeve 56 to its original position around the inner sleeve 58 to retract the locating wings 64 on the distal end 63 of the inner sleeve 58. While continuing to hold the plunger 54 in a fixed position relative to the incision to retain the vessel plug 52 at the desired depth, the outer and inner sleeves 56 and 58 of the insertion assembly 50 are withdrawn from the incision and from around the vessel plug 52 as shown in FIGS. 9 and 10. The overall length of the plunger member 54 and the vessel plug 52 are chosen so that as the proximal end of the inner sleeve 54 reaches the proximal member 74 on the plunger member 54, a sufficient amount of the vessel plug 52 will extend distally beyond the insertion assembly 50 so that the insertion assembly 50 may then be withdrawn from the incision while the distal end 68 of the vessel plug 52 is frictionally retained in the desired position in the incision.

The locating wings 64 of the present embodiment serve to provide a minimal amount of resistance as the insertion assembly 50 is moved to the desired location along the inner lumen of the blood vessel 70. It is anticipated that the locating wings 64 may be actuated by nearly any actuation mechanism as long as the locating wings 64 are retractable and provide sufficient resistance at the inner lumen of the blood vessel 70 to signal the user that the insertion assembly 50 is in the proper position for the insertion of the vessel plug 52 into the incision.

As with the prior embodiment, the distal end 68 of the vessel plug 52 is positioned in the incision at or adjacent to the outer lumen of the blood vessel 70 so that none of the vessel plug 52 extends into the blood vessel 70 to disrupt the flow of blood therethrough. The porosity of the vessel plug 52 is chosen so that the vessel plug 52 will expand as it absorbs fluids from the surrounding tissue and so that the vessel plug 52 will degrade in a matter of weeks or months. Because the vessel plug 52 does not extend into the lumen of the blood vessel 70, the vessel plug 52 of the present embodiment may include a clotting agent incorporated therein to promote localized hemostasis in the incision without increasing the likelihood of thrombosis formation in the blood vessel 70.

While the preferred forms of the present invention are described and illustrated herein, it will be obvious to those skilled in the art that various changes and modifications may be made thereto without departing from the scope of the present invention as defined by the following claims.

What is claimed is:
1. A closure device for sealing an incision formed in the body of a patient wherein the incision extends from the skin of the patient into a target organ or blood vessel of the patient, said closure device including a plug means comprising:

an elongate vessel plug having distal and proximal ends and said vessel plug is dimensioned to be received in the incision such that said distal end is located at a first predetermined position in the incision adjacent to the outer surface of the target organ or blood vessel of the patient and said proximal end is positioned adjacent to the epidermal layer of the skin of the patient;

an elongate positioning means associated therewith for positioning said distal end of said vessel plug in said first predetermined position; and wherein said positioning means includes a manually actuatable location member thereon and said locating member being movable between a first position wherein said locating member is generally coplanar with said positioning means and a second position wherein at least a portion of said locating member extends laterally from said positioning means.

2. A closure device for sealing an incision formed in the body of a patient wherein the incision extends from the skin of the patient into a target organ or blood vessel of the patient, said closure device including a plug means comprising:

an elongate vessel plug having distal and proximal ends and said vessel plug is dimensioned to be received in the incision such that said distal end is located at a first predetermined position in the incision adjacent to the outer surface of the target organ or blood vessel of the patient and said proximal end is positioned adjacent to the epidermal layer of the skin of the patient;

an elongate positioning means including a locating member for positioning said distal end of said vessel plug in said first predetermined position; and wherein said vessel plug is preloaded in said positioning means such that said distal end of said vessel plug is generally aligned in the incision by said locating member and said locating member is movably positioned near the distal end of said positioning means.

3. The closure device of claim 2 wherein said proximal end of said positioning means includes a plunger means associated therewith and said plunger means is longitudinally movable with respect to said positioning means to allow for the removal of said positioning means from the incision or puncture without dislocation of said vessel plug from said first predetermined positioned in the incision.

4. A closure device for sealing an incision formed in the body of a patient wherein the incision extends from the skin of the patient into a target organ or blood vessel of the patient, said closure device including a plug means comprising:

an elongate vessel plug having distal and proximal ends and said vessel plug is dimensioned to be received in the incision such that said distal end is located at a first predetermined position in the incision adjacent to the outer surface of the target organ or blood vessel of the patient and said proximal end is positioned adjacent to the epidermal layer of the skin of the patient;

an elongate positioning means associated therewith for positioning said distal end of said vessel plug in said first predetermined position; and wherein said vessel plug includes an elongate outer surface and said positioning means extends longitudinally adjacent to and along at least a portion of said vessel plug and said positioning means includes a distal end having an inflatable member thereon for positioning said distal end of said vessel plug in said first position.

5. The closure device of claim 4 wherein said positioning means removably extends longitudinally along said outer surface of said vessel plug and comprises an elongate balloon catheter.

6. A closure device for sealing an incision formed in the body of a patient wherein the incision extends generally from the skin of a patient into a target organ or blood vessel of the patient, said closure device comprising in combination:
an elongate insertion assembly having distal and proximal ends and a locating means adjacent said distal end and an actuation means associated therewith wherein actuation of said actuation means moves said locating means from a first position wherein said locating means is generally longitudinally aligned with said insertion assembly to a second position wherein at least a portion of said locating means extends generally laterally from said positioning means, and
a biodegradable and generally elongate vessel plug adapted to be positioned in a first predetermined position in said insertion assembly and wherein said vessel plug is further adapted to be retained in a second predetermined position in the incision in the patient.

7. The closure device of claim 6 wherein said insertion assembly comprises an inner and an outer elongate sleeve member wherein said outer sleeve member movably surrounds said inner sleeve member.

8. The closure device of claim 6 wherein said vessel plug is an elongate and generally rod-shaped member having distal and proximal ends and said distal end is contoured to conform to the outer surface of the target organ or blood vessel of the patient.

9. The closure device of claim 8 wherein a plunger means is operatively associated with said positioning means to contact said proximal end of said vessel plug, said plunger means being slidably movable in said positioning means to assist in moving said vessel plug from said first position in said insertion assembly to said second position in the incision.

10. A closure device for sealing an incision formed in the body of a patient wherein the incision extends generally from the skin of the patient into a target organ or blood vessel of the patient, said closure device comprising in combination:
a generally elongate vessel plug having distal and proximal ends adapted to be inserted into the incision of the patient such that said distal end of said vessel plug is shaped to generally conform to the outer surface of the target organ or blood vessel of the patient and said proximal end is adapted to be received in the incision generally adjacent to the outer surface of the skin of the patient, and
an insertion means having proximal and distal ends and said proximal end including an actuation means associated therewith and said distal end including an radial expansion means associated therewith wherein actuation of said actuation means increases the radial circumference of said expansion means to facilitate the placement of said distal end of said vessel plug in the incision.

11. The closure device of claim 10 wherein said insertion means comprises a balloon catheter having an expansion means comprised of an inflatable balloon on said distal end thereof.

12. The closure device of claim 10 wherein said vessel plug includes an elongate outer surface and said insertion means is operatively associated with said outer surface such that said distal end of said insertion means is operatively positionable adjacent said distal end of said vessel plug and said proximal end of said insertion means is operatively positionable proximally of said proximal end of said vessel plug.

13. A method of sealing an incision formed in the body of a patient wherein the incision extends generally from the skin of the patient into a target organ or blood vessel of the patient, the method comprising:
inserting an insertion assembly having distal and proximal ends and an actuatable and radially expansible locating means thereon into the incision in the patient;
actuating the locating means on the insertion assembly to actuate movement of the locating means from a first position on the insertion assembly to a second position wherein the circumference of the distal end of the insertion assembly is larger when the location means is in the second position then in the first position;
moving the insertion assembly to a predetermined position in the incision in the patient until the locating means contacts a predetermined portion of the target organ or blood vessel in the patient; and
positioning a vessel plug in the incision in the patient in accordance with the location determined by contact between the locating means and a portion of the target organ or blood vessel of the patient.

14. The method according to claim 13 further including the steps of actuating the movement of the locating means from the second position to the first position while maintaining the vessel plug in the position in the incision determined by the contact between the locating means and a portion of the target organ or blood vessel of the patient while removing the insertion assembly from the incision.

15. The method according to claim 14 further including the step of positioning a plunger member against the vessel plug to retain the vessel plug in the determined position in the incision as the insertion assembly is withdrawn from the incision.

16. The method according to claim 13 further including actuating an actuation means on the proximal end of the insertion assembly to actuate movement of the locating means from the first position to the second position to position the vessel plug in the position in the incision determined by the contact between the locating means and the target organ or blood vessel.

17. The method according to claim 13 further including the step of advancing the vessel plug in the incision until the distal end of the vessel plug contacts at least a portion of the locating means to position the vessel plug in the incision in the position determined by contact between the locating means and the target organ or blood vessel.

18. A method of sealing an incision formed in the body patient wherein the incision extends generally from the skin of the patient into a blood vessel of the patient, the method comprising:
inserting a relatively small diameter balloon catheter into the previously formed incision in the patient;
inflating a balloon on the distal end of the balloon catheter;

withdrawing the balloon catheter from the incision until the balloon contacts a predetermined portion of the inner lumen of the blood vessel;

inserting a vessel plug into the incision until the distal end of the vessel plug contacts the balloon on the balloon catheter;

deflating the balloon on the balloon catheter and removing the balloon catheter from the incision while the vessel plug is retained in the incision.

19. A method of sealing an incision formed in the body of a patient wherein the incision extends generally from the skin of the patient into a blood vessel of the patient, the method comprising the steps of:

inserting an insertion assembly having distal and proximal ends with a radially movable locating member along the distal end thereof and a plunger member associated with the proximal end thereof into the incision in the patient;

manually actuating the movement of the locating member laterally along the distal end of the insertion assembly to increase the radial diameter of the distal end of the insertion assembly;

withdrawing the insertion assembly from the incision until the locating member contacts the inner lumen of the blood vessel;

returning the locating member to the original reduced diameter position and withdrawing the insertion assembly from the incision while maintaining the vessel plug in the desired predetermined position in the incision by contacting the plunger member on the insertion assembly and withdrawing the insertion assembly towards the plunger member; and completely withdrawing the insertion assembly and the plunger member from the incision as the vessel plug is retained in the incision.

* * * * *